United States Patent [19]

Kopp et al.

[11] 4,412,553

[45] Nov. 1, 1983

[54] DEVICE TO CONTROL THE TRANSMEMBRANE PRESSURE IN A PLASMAPHERESIS SYSTEM

[75] Inventors: Clinton V. Kopp; James Hitchcock, both of Barrington, Ill.

[73] Assignee: Baxter Travenol Laboratories, Inc., Deerfield, Ill.

[21] Appl. No.: 277,449

[22] Filed: Jun. 25, 1981

[51] Int. Cl.³ .............................................. B01D 31/00
[52] U.S. Cl. ...................................... 137/118; 137/82; 137/87; 210/137; 210/433.2; 210/637; 251/61.1
[58] Field of Search ............................ 137/82, 87, 118; 251/61.1; 210/137, 321.1, 433.2, 637, 645, 646, 651

[56] References Cited

U.S. PATENT DOCUMENTS

| | | | |
|---|---|---|---|
| 3,052,064 | 9/1962 | Kaeser | 251/61.1 X |
| 3,057,376 | 10/1962 | Agutter | 251/61.1 X |
| 3,150,674 | 9/1964 | Connaught | 137/82 |
| 3,791,397 | 2/1974 | Janu | 137/82 |
| 3,929,148 | 12/1975 | Midy | 137/82 X |
| 4,303,068 | 12/1981 | Zelman | 210/637 X |
| 4,315,520 | 2/1982 | Atkinson | 137/82 |

FOREIGN PATENT DOCUMENTS 796476 1/1981 U.S.S.R. ............................... 137/82

Primary Examiner—Robert G. Nilson
Attorney, Agent, or Firm—Paul C. Flattery; Daniel D. Ryan

[57] ABSTRACT

A fluid flow control device comprises first second, and third fluid pathways. The first and second pathways are adapted for communication with separate sources of pressurized fluid. The third pathway is coupled in flow communication with the first pathway and includes a flexible wall which forms an interface with a portion of the second pathway. The flexible wall meters the flow communication between the first and third pathways in response to fluid pressure fluctuations in the second pathway. The fluid pressure in the first pathway is thereby elevated until substantial equilibrium with the fluid pressure in the second pathway occurs, and is thereafter continuously adjusted in response to subsequent fluctuations of fluid pressure in the second pathway to maintain this condition of substantial equilibrium.

5 Claims, 6 Drawing Figures

DEVICE TO CONTROL THE TRANSMEMBRANE PRESSURE IN A PLASMAPHERESIS SYSTEM

FIELD OF THE INVENTION

This invention generally relates to fluid flow control devices, and, more particularly, to fluid flow control devices which serve to control fluid pressures.

OBJECTS OF THE INVENTION

It is one of the principal objects of this invention to provide a fluid flow control device which is adapted for use in any system in which the control of fluid pressure is desirable, which operates with a minimum of moving parts, which lends itself to relatively efficient and inexpensive manufacturing techniques, and which can comprise any essentially disposable unit.

SUMMARY OF THE INVENTION

To achieve these and other objects, the invention provides a fluid flow control device which comprises first conduit means adapted for communication with a first source of pressurized fluid and second conduit means adapted for communication with a second source of pressurized fluid. The device further includes third conduit means in flow communication with the first conduit means for conducting the pressurized fluid from the first conduit means. The third conduit means includes generally flexible first wall means forming an interface with a portion of the second conduit means. The first wall means is operative in response to fluid pressures in the second conduit means for metering the flow communication between the first and third conduit means. The metering action of the flexible first wall means adjusts the fluid pressure in the first conduit means until it achieves substantial equilibrium with the fluid pressure then existent in the second conduit means, and thereafter maintains this state of substantial equilibrium, notwithstanding subsequent fluctuations in the pressure in the second conduit means.

In accordance with one embodiment, the device includes means for maintaining constant flow communication between the first and third fluid conduit means, despite the continuous metering action of the flexible first wall means.

In accordance with one embodiment, the device comprises a compact housing which is internally compartmentalized into the above described first, second and third conduit means in a manner which lends itself to efficient manufacture from plastic materials suited for contact with parenteral fluids and the like.

Other features and advantages of the invention will be pointed out in, or will be apparent from, the specification and claims, as will obvious modifications of the embodiments shown in the drawings.

Figure 1:
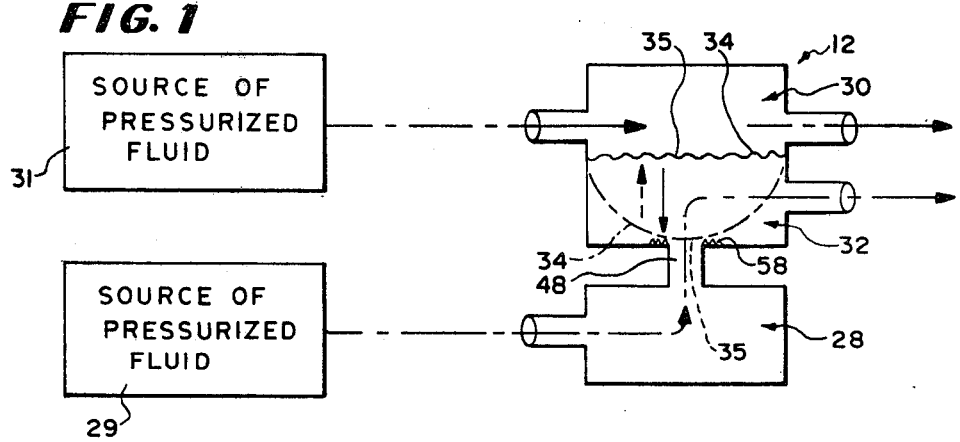
FIG. 1 is a diagrammatic view of a fluid flow control device which embodies various of the features of the invention.

Before explaining the embodiments of the invention in detail, it is to be understood that the invention is not limited in its application to the details of construction and the arrangement of components set forth in the following description and as illustrated in the drawings. The invention is capable of other embodiments and of being practiced and carried out in various ways. Also, it is to be understood that the phraseology and terminology used herein is for the purpose of description and should not be regarded as limiting.

DESCRIPTION OF THE PREFERRED EMBODIMENT

A fluid flow control device 12 is shown in FIG. 1. As will soon become apparent, the device 12 is applicable for use in a number of diverse environments in which it is desirable to control the flow of pressurized fluids for whatever reasons.

As is shown in FIG. 1, the device 12 includes conduit means defining first, second and third fluid pathways, respectively 28, 30, and 32. The first and second fluid pathways 28 and 30 are each individually adapted to communicate with its own source 29 and 31 of pressurized fluid to conduct pressurized fluid from the respective source 29 and 31. The third fluid pathway 32 is in flow communication with the first fluid pathway 28 to conduct pressurized fluid therefrom.

In addition, the third fluid pathway 32 includes first wall means 34 which forms an interface with a portion of the second fluid pathway 30. The first wall means 34 is made of a flexible material and is operative in response to the fluid pressure in the second fluid pathway 30 for movement (as is generally shown by the use of arrows and phantom lines in FIG. 1) to meter the flow communication between the first and third fluid pathways 28 and 31.

More particularly, in response to an initial condition in which the fluid pressure in the second pathway 30 exceeds the fluid pressure in the first pathway 28, the first wall means 34 is moved to restrict the flow of fluid between the first and third pathways 28 and 32. This serves to elevate the fluid pressure in the first pathway 28 until a condition of substantial equilibrium between the fluid pressures in the first and second pathways 28 and 30 occurs. Thereafter, the first wall means 34 is operative in response to subsequent fluctuations in the fluid pressure in the second pathway 30 to maintain a condition of substantial equilibrium between the two fluid pressures.

The device 12 as heretofore described may be variously constructed, depending upon the particular operative environment in which use is contemplated. In the embodiment illustrated in FIGS. 2 through 4, the device 12 comprises a compact housing 36 enclosing an interior area 38. The interior area 38 is itself compartmentalized by spaced wall means 40 into the three fluid pathways 28, 30, and 32 heretofore described.

Figure 3:
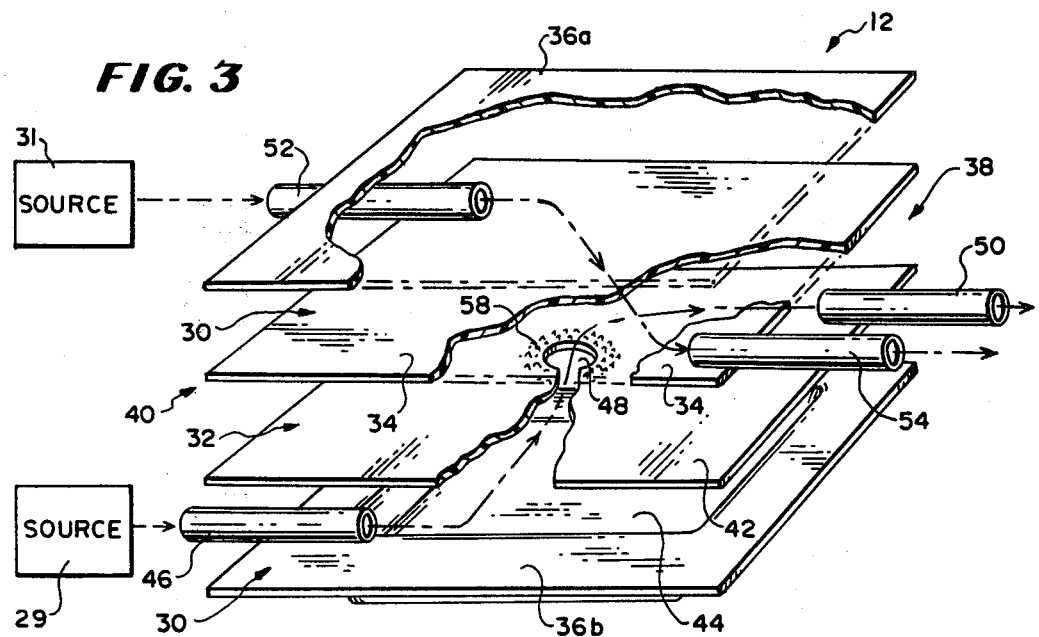
FIG. 3 is an exploded perspective view of the device shown in FIG. 2, with parts broken away to show the flow of fluids through the device.
Figure 4:
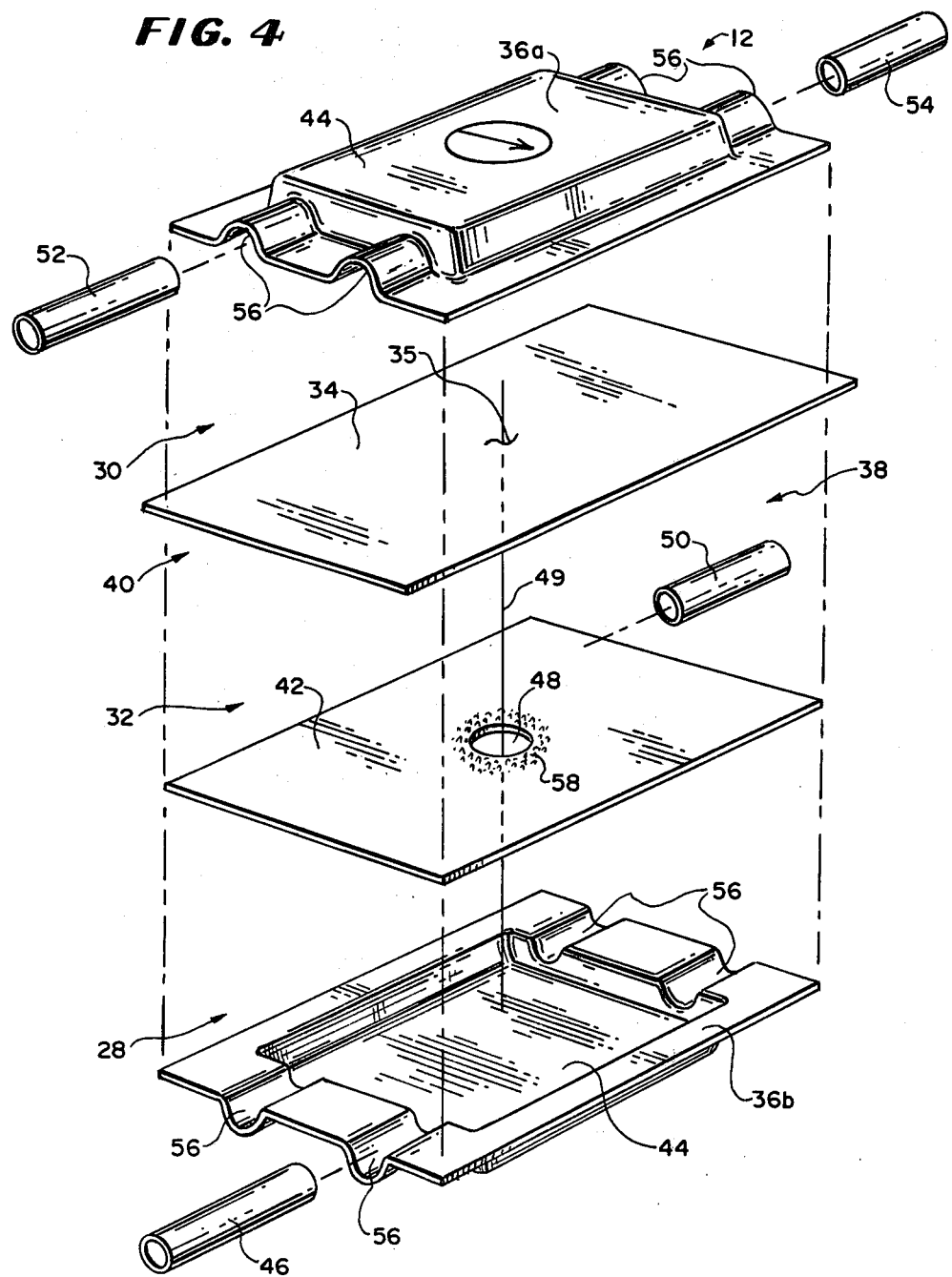
FIG. 4 is another exploded perspective view of the component parts of the device shown in FIG. 2.

More particularly (and as best seen in FIGS. 3 and 4), the wall means 40 includes the previously described first wall means 34 which forms the flexible interface between the second and third fluid pathways 30 and 32 within the housing interior 38. The wall means 40 also includes second wall means 42, which forms an interface between the first and third fluid pathways 28 and 32.

In this arrangement, the three fluid pathways 28, 30 and 32 extend in a generally parallel and stacked relationship one above the other within the housing interior 38, as can be seen in FIG. 3. The third fluid pathway 32 is positioned between the first and second pathways 28 and 30, which are themselves spaced at opposite ends of the interior area 38. By virtue of the raised exterior portions 44 of the housing 36, the enclosed portions of the first and second pathways 28 and 30 can be viewed as defining oppositely spaced chambers within the housing interior 38.

The first pathway 28 includes an inlet portion 46 which extends outwardly of the housing 36 and which is adapted for communication with the source 29 of pressurized fluid. The second wall means 42 is provided with an opening 48 which, in the illustrated embodiment, extends generally at a right angle to the fluid flow path through the first pathway 28 and which provides the heretofore described flow communication between the first and third fluid pathways 28 and 32. In this respect, the opening 48 serves as an outlet portion for the first fluid pathway 28 and an inlet portion for the third fluid pathway 32. The third fluid pathway 32 further includes an outlet portion 50 which extends outwardly of the housing 36 and which communicates with the atmosphere.

As can be seen in FIG. 3, the flow of pressurized fluid from the source 29 enters the housing 36 through the inlet portion 46 of the first fluid pathway 28, and then proceeds through the opening 48 to exit the housing 36 through the outlet portion 50 of the third fluid pathway 32 subject, of course, to metering by the flexible first wall means 34.

The second fluid pathway 30 includes spaced, generally coplanar inlet and outlet portions, respectively 52 and 54, both of which extend outwardly of the housing 36. The inlet portion 52 is adapted for communication with the source 31 of pressurized fluid, and the outlet portion 54 communicates with the atmosphere.

As can also be seen in FIG. 3, the pressurized fluid from the source 31 flows in an essentially laminar path into and out of the second fluid pathway 30.

This compact structural arrangement lends itself to construction utilizing a relatively few preformed parts. It also lends itself to construction utilizing only plastic materials and the like which have been approved for contact with human blood or other parenteral fluids. Furthermore, the device 12 can be manufactured in an efficient and economical manner and constitute an essentially disposable unit.

For example, in the illustrated embodiment (see FIG. 4), the housing 36 includes upper and lower housing portions, respectively 36a and 36b, which can be manufactured from a suitable plastic material, such as by the use of injection molding techniques. Preferably, the upper and lower housing portions 36a and 36b are generally rigid or semirigid in construction and include a spaced pair of outwardly bowed or convex grooves 56 formed at each opposite end.

The second wall means 42 constitutes a presized sheet of suitable and preferably flexible plastic material, in which the opening 48 is centrally located. The first wall means 34 comprises a presized sheet of flexible plastic material having a thickness of approximately 15 mils.

To form the desired compartmentalization within the housing 36 (and as best seen in FIGS. 3 and 4), the inlet portion 46 of the first fluid pathway 28 comprises a presized section of plastic polyvinyl chloride tubing which is sandwiched between the lower housing portion 36b and the second wall means 42. The grooves 56 of the upper and lower housing portions 36a and 36b together form a bushing to receive the inlet tubing portion 46 (see FIG. 2).

The inlet and outlet portions 52 and 54 of the second fluid pathway 30 likewise comprise identical presized sections of plastic polyvinyl chloride tubing positioned diagonally across from each other and sandwiched between the upper housing portion 36a and the flexible sheet comprising the first wall means 34. This diagonal relationship between the tubing portions promotes a uniform, laminar flow of fluid through the second fluid chamber 30.

As before, the grooves 56 of the upper and lower housing portions 36a and 36b together form bushings to receive the inlet and outlet tubing portions 52 and 54.

In similar fashion, the outlet portion 50 of the third fluid pathway 32 can comprise a presized section of plastic polyvinyl chloride tubing which is positioned generally diagonally across from the tubing forming the inlet portion 46 of the first fluid pathway 28 and sandwiched between the flexible first wall means 34 and the second wall means 42 and within the bushings formed by the cooperating grooves 56. The diagonal relationship between these tubing portions 30 and 46 promotes a uniform and laminar flow of fluid into and out of the first and third fluid pathways 28 and 32 through the interconnecting opening 48.

Figure 2:
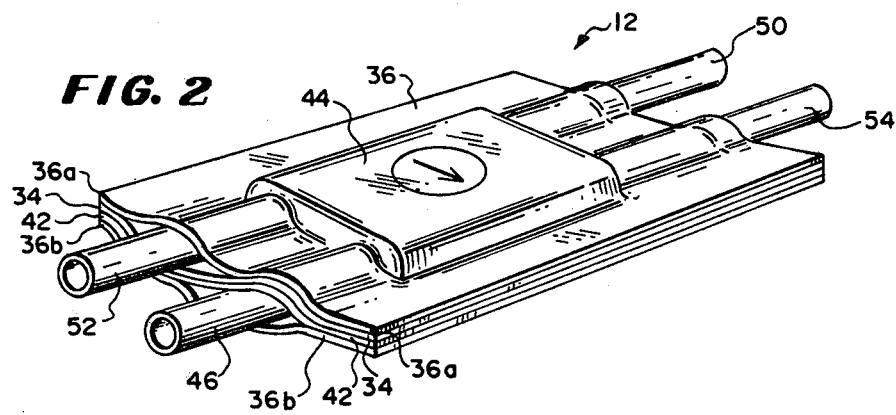
FIG. 2 is a perspective view of one embodiment of the pressurized fluid flow control device shown in FIG. 1.

The entire assembly shown in FIG. 4 can be sandwiched together into the compact configuration shown in FIG. 2 and peripherally sealed, such as by the use of radio frequency, heat, or solvent sealing methods. During such manufacture, the peripheries of the flexible first and second wall means 34 and 42 will conform to sealingly accommodate the adjacent tubing portions.

As can be best seen in FIGS. 3 and 4, the flexible first wall means 34 is generally oppositely spaced in facing relationship from the opening 48 formed in the second wall means 42. Furthermore, the axis 49 of the opening 48 (see FIG. 4) is generally aligned with the midportion 35 of the first wall means 34. Because of this construction, coupled with the inherent flexibility of the first wall means 34, the first wall means 34 is operative for movement in response to fluid pressures in a path along the axis 49 toward and away from the opening 48.

More particularly, in response to an initial condition in which the fluid pressure in the second fluid pathway 30 exceeds the fluid pressure in the first fluid pathway 28 (and, hence, in the third fluid pathway 32 as well), the flexible first wall means 34 will respond by moving in its axial path from a preexisting initial position (which is shown in solid lines in FIG. 1) toward the opening 48. This movement is generally shown by arrows in FIG. 1.

As can be seen in FIG. 1, the movement of the flexible wall means 34 in its axial path toward the opening 48 results in a change in the configuration of the flexible first wall means 34 from its preexisting condition (shown in solid lines in FIG. 1) toward a generally convex configuration outwardly bowed into the third fluid pathway 32 (shown in phantom lines in FIG. 1).

Closer proximity of the flexible first wall means 34, and, in particular, its midportion 35, to the opening 48 serves to restrict the flow of fluid through the opening 48. This restriction, in turn, causes the fluid pressure in the first fluid pathway 28 to rise. This elevation in the pressure in the first fluid pathway 28 will continue until pressure equalization with the then prevailing fluid pressure in the second pathway 30 occurs.

It should be appreciated that the particular configuration the flexible wall means 34 will assume within the third pathway 32 and relative to the opening 48 to meter the flow communication through the opening 48 and bring about pressure equalization will depend upon the particular magnitudes of the then prevailing pressures in the first and second pathways 28 and 30, as well as the then prevailing fluid flow rates through the first and second pathways 28 and 30.

Should the fluid pressure in the second fluid pathway 30 subsequently increase or decrease, the flexible wall means 34 will correspondingly change its configuration by moving in its axial path toward a new position, respectively, closer to or farther away from the opening 48. This automatically changes the previously imposed restriction to the fluid flow between the first and third fluid pathways 28 and 32 in lieu of a new restriction. The flow communication between the first and third pathways 28 and 32 will be metered at a new rate until the fluid pressure in the first pathway 28 achieves equalization at the higher or lower pressure level.

The flexible first wall means 34 is thus movable in its axial path through a range of positions which are progressively spaced closer to or farther from the opening 48. The particular position and configuration of the flexible wall means 34 within this range will depend upon the particular fluid pressures and flow rates then prevailing.

It should be appreciated that the movement of the flexible wall means 34 as just described occurs virtually instantaneously with pressure fluctuations occurring within the second fluid pathway 30. Thus, the device 12 is operative to continuously maintain pressure equilibrium between the two fluid pathways 28 and 30.

It should also be appreciated that the device 12 operates without the use of valve seats or the like. Thus, movement of the flexible wall means 34 toward the opening 48 will not normally serve to completely close the opening 48, and thereby completely block flow communication therethrough. The device 12 is thus operative for use in situations where a continuous, uninterrupted flow of fluid into and through the first and third fluid pathways 28 and 32 is desired.

Furthermore, in the illustrated and preferred embodiment, the area 58 circumferentially surrounding the opening 48 is roughened or scored to break any surface tension that might develop between the area 58 and the flexible first wall means 34. This positively assures that the flexible wall means 34 will not assume a position completely blocking the opening 58, and that a constant flow of fluid between the first and third pathways 28 and 32 is maintained regardless of the pressures and flow rates encountered and the corresponding relative configuration of the flexible first wall means 35.

Figure 5:
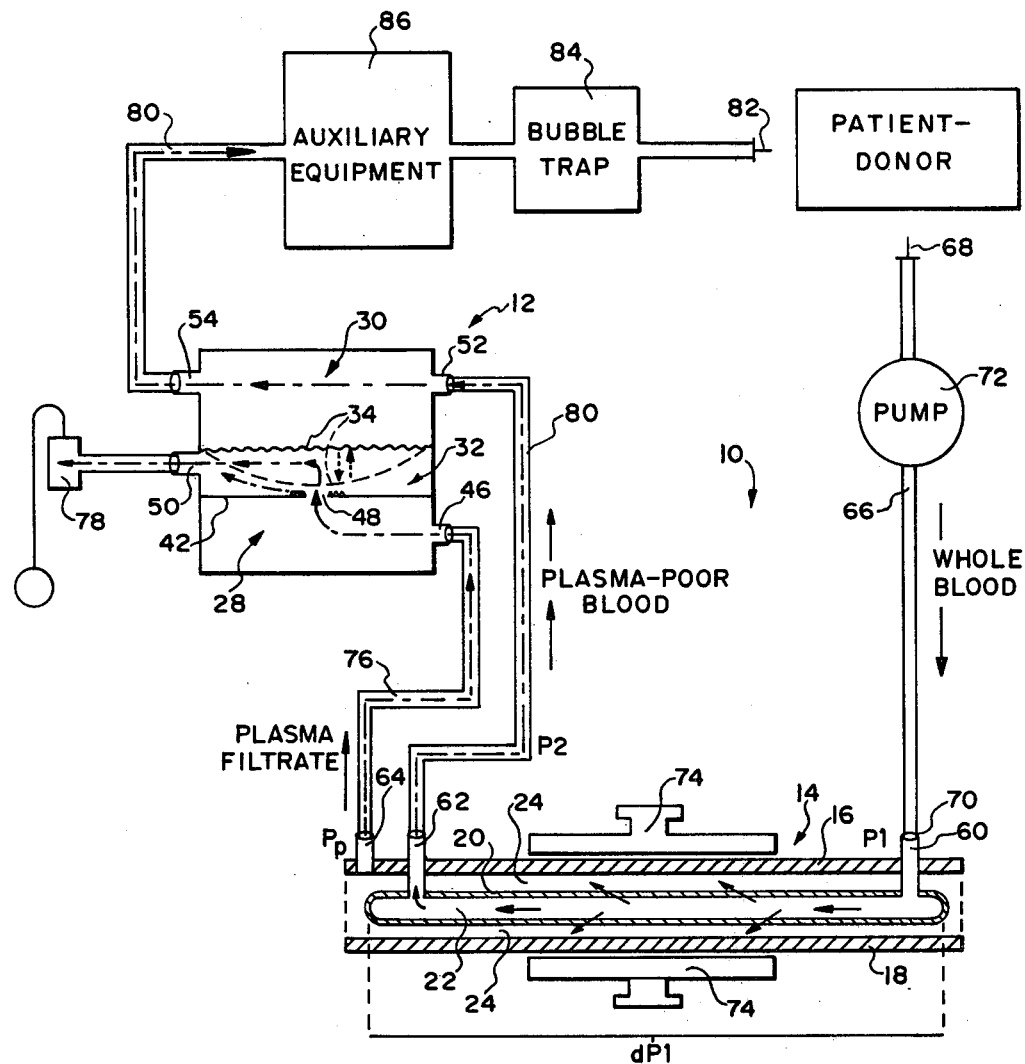
FIG. 5 is a diagrammatic view of the fluid flow control device shown in FIGS. 2 through 4 in association with a membrane plasmapheresis apparatus utilizing spacedapart sheets of microporous membranes.

As shown in FIG. 5, the fluid flow control device 12 as heretofore described is applicable for use in association with a membrane plasmapheresis apparatus 10 which is operative for removing, or "harvesting" the plasma from whole blood for exchange, transfusion, or fractionation purposes.

As shown in FIG. 5, the apparatus 10 includes a module or cell 14 in which microporous membranes are housed. Various membranes can be used, provided that they have a pore size suited for separating the plasma from whole blood, given the proper conditions of pressure and flow rates across the membrane surfaces.

The module 14 itself may also be variously constructed, according to the membrane configuration utilized. Two alternate embodiments are shown, respectively, in FIGS. 5 and 6. It should be appreciated, however, that numerous other embodiments are possible.

In the embodiment shown in FIG. 5, the module 14 includes first and second generally planar members, respectively 16 and 18, defining a housing in which two sheets of a microporous membrane 20 having a pore size of about 0.1 micron to 2 microns are positioned in a facing, spaced-apart relationship. A fluid path 22 is thus formed between the membranes 20, and the module 14 includes an inlet and outlet port, respectively 60 and 62, communicating at opposite ends of the fluid path 22. Open volumes 24 are also formed between the outer surfaces of the membranes 20 and the interior surfaces of the planar members 16 and 18, and the module 14 includes an outlet port 64 communicating with the volumes 24.

Figure 6:
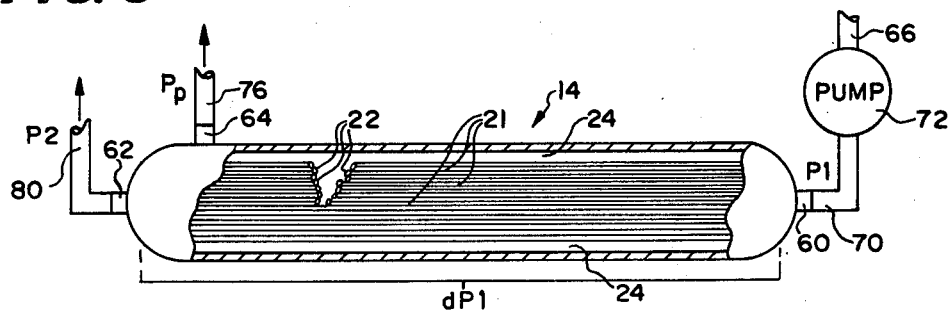
FIG. 6 is a perspective and partially diagrammatic view of a module in which a cluster of hollow fiber membranes are supported and which is adapted for use with the membrane plasmapheresis apparatus shown in FIG. 5.

In the alternate embodiment shown in FIG. 6, the module 14 takes the form of a generally tubular housing in which a cluster of individual hollow fiber membranes 21 is supported. The hollow fiber membranes 21 can be fabricated from various materials, for example, polypropylene having a maximum pore size of about 0.6 microns and an average pore size in the neighborhood of 0.3 microns. The hollow bore of each fiber 21 defines the fluid path 22 corresponding to the one heretofore described with respect to the FIG. 5 embodiment. The tubular housing is constructed so as to form an open volume 24 circumferentially enveloping the hollow fiber cluster. As in the FIG. 1 embodiment, the module 14 includes inlet port 60 and outlet ports 62 and 64.

The apparatus 10 also includes a whole blood inlet conduit 66 having at one end thereof a phlebotomy needle 68 for insertion into the arm of a patient-donor. The other end 70 of the conduit 66 is attached to the inlet port 60 of the module 14.

The apparatus 10 further includes an in-line pump 72, for example, a peristaltic pump, which delivers whole blood from the patient-donor to the inlet port 60 of the module 14 subject to a predetermined inlet pressure which is under the control of the operator. The inlet pressure will hereafter be referred to and is shown in FIGS. 5 and 6 as P1.

As the whole blood traverses the length of the fluid pathway 22, a predetermined pressure drop occurs. This pressure drop is symbolized as dP1 in FIGS. 5 and 6. The size of the pressure drop dP1 depends principally upon the fluid volume of the pathway 22, which, in the FIG. 5 embodiment, depends in large part upon the lateral spacing between the sheet membranes 20. This lateral spacing is controlled by use of an adjustable clamp 74, which presses the planar members 16 and 18 together to achieve the desired pressure drop dP1.

In the FIG. 6 embodiment, the interior diameter of the hollow bore of each hollow fiber 21 is preselected to achieve the desired pressure drop, obviating the need for the clamp 74.

By carefully controlling the magnitudes of the inlet pressure P1 and the pressure drop dP1, the whole blood is subjected to a desired sheer rate as it traverses the membranes 20 or 21. This causes the red cells, leukocytes, and platelets to proceed in a laminar path across the membranes 20 or 21. At the same time, a determinable transmembrane pressure, or TMP, is generated, which, when within the operationally desirable limits of between approximately 50 mmHg to 100 mmHg, acts as a driving force to cause only the plasma to pass through the pores of the membranes 20 or 21 and into the volumes 24. However, as will be discussed in greater detail later herein, should the transmembrane pressure exceed a critical level (approximately 120 mmHg), hemolysis can occur.

To conduct the plasma filtrate from the module 14, the apparatus 10 includes a collection conduit 76 attached to the outlet port 64 in flow communication with the plasma filtrate volumes 24. The conduit 76 has an end connection to a plasma filtrate collection bag 78. Typically, this plasma filtrate is subject to a pressure (Pp in FIGS. 5 and 6) which is at or near atmospheric pressure, or $\phi$ mmHg.

To conduct the cellular components which do not pass through the membranes 20 or 21 from the module 14, these components now being collectively referred to as plasma-poor blood, the apparatus 10 includes a transfusion set 80 attached to the outlet port 62. The transfusion set 80 includes a phlebotomy needle 82 for insertion into the patient-donor to return the conducted plasma-poor blood to the patient-donor.

A bubble trap 84 is preferably connected in line with the transfusion set 80 between the outlet port 62 and the needle 82. Auxiliary equipment (generally designated by the numeral 86 in FIG. 5), such as a blood warmer, can also be connected in line with the transfusion set 80 to enhance the conduction of plasma-poor blood back to the patient-donor.

It has been observed that, when the various operationally necessary or desirable equipment are positioned in the flow path of the plasma-poor blood downstream of the module 14 (i.e., the transfusion set 80, the needle 82, and any auxiliary equipment 86), a resistance to the return of the plasma-poor blood is generated. This resistance will hereafter be identified as the backside pressure (symbolized as P2 in FIGS. 5 and 6). Also contributing to the magnitude of the backside pressure P2 is the blood pressure of the individual patient-donor, as well as any random movement of patient donor's arm during the procedure, which can cause a temporary occlusion in the flow path. The magnitude of the backside pressure P2 is often significant and can suddenly and randomly fluctuate during the course of the procedure between 20 mmHg and 150 mmHg.

It has also been observed that these sudden and random fluctuations in the backside pressure P2, if not compensated for, serve to induce correspondingly sudden and random variations in the transmembrane pressure of the apparatus 10. Thus, the presence of equipment downstream of the module 14 causes the transmembrane pressure to be unstable and can lead to sudden and random elevations of the transmembrane pressure above operationally desirable levels to a magnitude above 120 mmHg. At this critical level, the red cells traversing the membranes 20 or 21 can themselves be driven into the pores of the membranes 20 or 21 and be torn, damaged, or destroyed. Hemolysis results.

Efforts can be made to stabilize the transmembrane pressure at operationally desirable levels by removing as many of the sources of the backside pressure P2 as possible. For example, the size of the phlebotomy needle 82 can be enlarged (the smaller the needle, the larger the pressure developed, and vice versa), but this, in turn, can lead to patient-donor discomfort. Or, the use of ancillary equipment 86 downstream of the module 14 can be minimized, but such equipment is desirable for an efficient plasmapheresis procedure. To deal with the problem, the operator can constantly adjust the elevation of the plasma collection bag 78, but such activities divert operator attention from other necessary duties. In short, efforts such as those detailed run counter to patient-donor comfort and an efficient membrane plasmapheresis procedure and indeed do not and cannot completely stabilize the transmembrane pressure. The blood pressure of the particular patient-donor, or any arm movement of the patient-donor during the procedure, are variables which simply cannot be anticipated and instantly compensated for.

The fluid flow control device 12 as heretofore described can be used in association with the apparatus 10 to effectively stabilize the transmembrane pressure at operationally desired levels, regardless of the presence of and fluctuations in the backside pressure P2.

In this environment, and as can be seen in FIG. 5, the fluid flow control device 12 as illustrated in FIGS. 2 through 4 is connected downstream of the module 14 in flow communication with both the transfusion set 80 and the plasma collection conduit 76. The inlet portion 46 of the first fluid pathway 28 is attached in direct flow communication with the plasma collection port 64, and the outlet portion 50 of the third fluid pathway 32 is attached in direct flow communication with the plasma collection container 78.

As a result of the interconnection in line with the plasma collection conduit 76, plasma filtrate flows out of the plasma volumes 24, subject to the plasma side pressure Pp, into and through the first and third fluid pathways 28 and 32, via the opening 48, and into the plasma collection container 78. This flow is generally shown by arrows in FIG. 5.

The inlet and outlet portions 52 and 54 of the second fluid pathway 30 are connected in line with the transfusion set 80 upstream of the bubble trap 84 and any associated auxiliary equipment 86.

As a result of this in-line connection (and as generally shown by arrows in FIG. 5), the plasma-poor blood flows from the outlet port 62 subject to the back pressure P2, into and through the laminar flow path of the second fluid pathway, and thence toward the downstream equipment. The laminar flow path provided by the second fluid pathway 30 minimizes undesirable mixing, or turbulence, of the blood during its return to the patient-donor. This, in turn, reduces the chance of hemolysis occasioned by such mixing.

At the outset of the plasmapheresis procedure, a pressure differential will always exist between the plasma pressure Pp (typically at $\phi$ mmHg) and the backside blood pressure P2 (typically between 20 mmHg and 150 mmHg). The flexible first wall means 34 will thus be immediately moved as heretofore described in its axial path toward the opening 48 to restrict the flow of plasma filtrate between the first and third fluid pathways 28 and 32. As the flow of plasma filtrate through the opening 48 is restricted, the plasma pressure Pp is successively elevated until substantial equilibrium is reached between Pp and P2 then existent. The device 12 will thereafter operate to maintain this equilibrium, notwithstanding subsequent variations in P2. The device 12 will also operate to maintain a continuous flow of plasma filtrate and plasma-poor blood downstream of the module 14.

While the fluid flow control device 12 of the present invention can be of various sizes, depending upon the particular environment in which use is contemplated, in one embodiment thereof suited for operation under the pressure conditions normally encountered during membrane plasmapheresis operations, the housing is approximately 2.5 inches in overall length (exclusive of the outwardly extending tubings), approximately 1.5 inches in overall thickness, with the three fluid flow pathways 28, 30 and 32 formed therein as heretofore described.

Use of this operative embodiment of the device 12 in association with the apparatus 10 has been observed to stabilize the transmembrane pressure, regardless of the magnitude of the then existent backside pressure P2, at a magnitude which represents only the flow resistance of the module 14 itself (or P1-dP1), which is a quantity under direct operator control. In particular, when an inlet pressure P1 of between 150 mmHg and 200 mmHg is maintained, along with a constantly maintained pressure drop dP1 across the module 14 of approximately 100 mmHg, the device 12 serves to stabilize the transmembrane pressure within the operationally desirable range of between 50 mmHg and 100 mmHg, even though the backside pressure P2 may at the same time be undergoing random fluctuations of between 20 mmHg and 150 mmHg.

In addition, the device 12 has been observed to continuously maintain an uninterrupted flow of plasma filtrate from the module 14 and through the first and third pathways 54 and 58 at a rate of between 10 cubic centimeters per minute and 80 cubic centimeters per minute. At the same time, the device 12 has been observed to continuously maintain an uninterrupted flow of plasma-poor blood from the module 14 and through the second pathway 56 at a rate of between 40 cubic centimeters per minute and 300 cubic centimeters per minute.

Use of the fluid flow control device 12 in association with the apparatus 10 also permits the use of operationally desirable components of membrane plasmapheresis, such as a smaller, more comfortable needle, and auxiliary equipment such as the blood warmer, without affecting the stability of the transmembrane pressure and without causing hemolysis.

It should be appreciated that various changes and modifications can be made without departing from the spirit of the invention or from the scope of the appended claims.

We claim:

1. A device for controlling the transmembrane pressure of a membrane which filters plasma from whole blood in a plasmapheresis system which includes a fluid line for conducting plasma-poor blood from the membrane to the donor and another fluid line for simultaneously conducting plasma filtrate from the membrane for collection, said device comprising:

an upper member and a lower member which are peripherally sealed together to collectively form a housing having an interior area, a generally flexible first interior wall and a second interior wall, said walls being peripherally sealed between the peripheries of said upper and lower members and positioned one atop the other within said interior area to compartmentalize said interior area into a first chamber, which extends between said upper member and said flexible first wall; a second chamber, which extends between said lower member and said second wall; and an interior fluid path, which extends between said flexible first wall and said second wall, first and second tubular members sealingly engaged between the peripheries of said upper member and said flexible first wall at diagonally opposite sides of said housing and extending from said first chamber outwardly of said housing along generally parallel and coplanar axes, said first and second tubular members communicating with the plasma-poor blood line for directing the plasma-poor blood in a uniform, laminar path across said first chamber, a third tubular member sealingly engaged between the peripheries of said lower member and said second wall and extending from said second chamber outwardly of said same housing side as said first tubular member along an axis which is generally parallel to the axis of said first tubular member, said third tubular member communicating with the plasma filtrate line for directing plasma filtrate into said second chamber, means defining an opening in said second wall essentially in the mid-portion thereof for directing the plasma filtrate from said second chamber into said interior fluid path, a fourth tubular member diagonally oppositely spaced from said third tubular member, said fourth tubular member being sealingly engaged between the peripheries of said first and second interior walls and extending from said interior fluid path outwardly of said housing along an axis which is generally parallel to the axis of said second tubular member, said fourth tubular member communicating with the plasma filtrate line for directing plasma filtrate out of said interior fluid path for collection, and said generally flexible first wall being operative for relative movement toward and away from said second wall opening to variably restrict the flow of plasma filtrate through said opening in response to pressure differentials between the plasma-poor blood in said first chamber and the plasma filtrate in said second chamber to establish and thereafter maintain substantial equilibrium between the pressure of the plasma filtrate and the pressure of the plasma-poor blood.

2. A device according to claim 1 and further including means defining a roughened area circumferentially surrounding said opening in said second wall for breaking surface tension between said second wall and said flexible first wall during movement of said flexible first wall, whereby plasma filtrate is constantly conducted through said opening, despite the restrictions imposed by said flexible first wall.

3. A device according to claim 1 or 2 wherein said upper and lower members each include grooves in diagonally opposite corners thereof, said grooves aligning when said upper and lower members are peripherally sealed together to form bushings to sealingly engage said first, second, third, and fourth tubular members.

4. A device according to claim 3 wherein said upper and lower members, said first and second walls, and said first, second, third, and fourth tubular members are made of plastic material approved for contact with human blood.

5. A device according to claim 3 wherein said upper and lower members each includes an outwardly raised center portion which increases the fluid volume of said associated chamber.

* * * * *